United States Patent
Artale

(10) Patent No.: US 11,207,128 B2
(45) Date of Patent: *Dec. 28, 2021

(54) SURGICAL INSTRUMENT WITH SYSTEM AND METHOD FOR SPRINGING OPEN JAW MEMBERS

(71) Applicant: COVIDIEN LP, Mansfield, MA (US)

(72) Inventor: Ryan C. Artale, Crested Butte, CO (US)

(73) Assignee: Covidien LP, Mansfield, MA (US)

(*) Notice: Subject to any disclaimer, the term of this patent is extended or adjusted under 35 U.S.C. 154(b) by 694 days.

This patent is subject to a terminal disclaimer.

(21) Appl. No.: 16/111,819

(22) Filed: Aug. 24, 2018

(65) Prior Publication Data

US 2018/0360526 A1 Dec. 20, 2018

Related U.S. Application Data

(63) Continuation of application No. 14/152,618, filed on Jan. 10, 2014, now Pat. No. 10,070,916.

(Continued)

(51) Int. Cl.
*A61B 18/14* (2006.01)
*A61B 17/28* (2006.01)
*A61B 18/00* (2006.01)

(52) U.S. Cl.
CPC ...... *A61B 18/1445* (2013.01); *A61B 17/2841* (2013.01); *A61B 2017/2845* (2013.01);
(Continued)

(58) Field of Classification Search
CPC ........... A61B 2018/00916; A61B 2018/00922; A61B 2018/0094; A61B 2018/00958;
(Continued)

(56) References Cited

U.S. PATENT DOCUMENTS 3,100,489 A    8/1963  Bagley
D249,549 S     9/1978  Pike
(Continued)

FOREIGN PATENT DOCUMENTS

CN   201299462 Y   9/2009
DE    2415263 A1  10/1975
(Continued)

OTHER PUBLICATIONS

European Search Report from Application No. EP14158818.6 dated May 28, 2014.

(Continued)

*Primary Examiner* — Ronald Hupczey, Jr.
(74) *Attorney, Agent, or Firm* — Carter, DeLuca & Farrell LLP

(57) ABSTRACT

A surgical instrument includes a housing and an elongated shaft operably coupled to an actuating mechanism moveable between an actuated position and an unactuated position. An end effector includes a pair of opposing first and second jaw members. One or more drive surfaces are disposed on the actuating mechanism and configured to compress a spring upon movement of the actuating mechanism to the actuated position. The spring imparts a spring force in a distal direction to bias the actuating mechanism to the unactuated position. An electrically conductive tissue sealing surface extends along a length of one or both of the jaw members and is adapted to connect to a source of electrosurgical energy.

20 Claims, 13 Drawing Sheets

Related U.S. Application Data

(60) Provisional application No. 61/776,159, filed on Mar. 11, 2013.

(52) U.S. Cl.
CPC ............. *A61B 2018/0063* (2013.01); *A61B 2018/00196* (2013.01); *A61B 2018/00345* (2013.01); *A61B 2018/00589* (2013.01); *A61B 2018/00595* (2013.01); *A61B 2018/00601* (2013.01); *A61B 2018/1455* (2013.01)

(58) Field of Classification Search
CPC ........ A61B 2018/1452; A61B 18/1445; A61B 18/1447; A61B 2017/2913; A61B 2017/2916; A61B 2017/2933; A61B 2017/2934; A61B 2017/2936
See application file for complete search history.

(56) References Cited

U.S. PATENT DOCUMENTS

| | | | |
|---|---|---|---|
| D263,020 S | | 2/1982 | Rau, III |
| 4,461,297 A | | 7/1984 | Sutter |
| 4,461,305 A | | 7/1984 | Cibley |
| D295,893 S | | 5/1988 | Sharkany et al. |
| D295,894 S | | 5/1988 | Sharkany et al. |
| D298,353 S | | 11/1988 | Manno |
| D299,413 S | | 1/1989 | DeCarolis |
| 5,122,139 A | | 6/1992 | Sutter |
| 5,211,655 A | | 5/1993 | Hasson |
| D343,453 S | | 1/1994 | Noda |
| D348,930 S | | 7/1994 | Olson |
| D349,341 S | | 8/1994 | Lichtman et al. |
| D354,564 S | | 1/1995 | Medema |
| 5,383,875 A | | 1/1995 | Bays et al. |
| D358,887 S | | 5/1995 | Feinberg |
| 5,454,827 A | | 10/1995 | Aust et al. |
| 5,478,351 A | * | 12/1995 | Meade ................ A61B 17/29 |
| | | | 606/174 |
| 5,512,721 A | | 4/1996 | Young et al. |
| 5,601,601 A | | 2/1997 | Tal et al. |
| D384,413 S | | 9/1997 | Zlock et al. |
| 5,746,739 A | | 5/1998 | Sutter |
| H1745 H | | 8/1998 | Paraschac |
| D402,028 S | | 12/1998 | Grimm et al. |
| D408,018 S | | 4/1999 | McNaughton |
| 5,891,140 A | | 4/1999 | Ginn et al. |
| 5,891,142 A | | 4/1999 | Eggers et al. |
| D416,089 S | | 11/1999 | Barton et al. |
| 6,010,516 A | | 1/2000 | Hulka |
| D424,694 S | | 5/2000 | Tetzlaff et al. |
| D425,201 S | | 5/2000 | Tetzlaff et al. |
| 6,083,150 A | * | 7/2000 | Aznoian ................ A61B 10/06 |
| | | | 600/564 |
| 6,106,542 A | | 8/2000 | Toybin et al. |
| 6,117,158 A | | 9/2000 | Measamer et al. |
| H1904 H | | 10/2000 | Yates et al. |
| D449,886 S | | 10/2001 | Tetzlaff et al. |
| D453,923 S | | 2/2002 | Olson |
| D454,951 S | | 3/2002 | Bon |
| D457,958 S | | 5/2002 | Dycus et al. |
| D457,959 S | | 5/2002 | Tetzlaff et al. |
| H2037 H | | 7/2002 | Yates et al. |
| 6,458,130 B1 | * | 10/2002 | Frazier ................ A61B 18/1445 |
| | | | 606/51 |
| D465,281 S | | 11/2002 | Lang |
| D466,209 S | | 11/2002 | Bon |
| D493,888 S | | 8/2004 | Reschke |
| D496,997 S | | 10/2004 | Dycus et al. |
| D499,181 S | | 11/2004 | Dycus et al. |
| D502,994 S | | 3/2005 | Blake, III |
| D509,297 S | | 9/2005 | Wells |
| D525,361 S | | 7/2006 | Hushka |
| 7,083,613 B2 | | 8/2006 | Treat |
| D531,311 S | | 10/2006 | Guerra et al. |
| D533,274 S | | 12/2006 | Visconti et al. |
| D533,942 S | | 12/2006 | Kerr et al. |
| D535,027 S | | 1/2007 | James et al. |
| 7,166,106 B2 | | 1/2007 | Bartel et al. |
| D538,932 S | | 3/2007 | Malik |
| D541,418 S | | 4/2007 | Schechter et al. |
| D541,611 S | | 5/2007 | Aglassinger |
| D541,938 S | | 5/2007 | Kerr et al. |
| 7,211,079 B2 | | 5/2007 | Treat |
| D545,432 S | | 6/2007 | Watanabe |
| D547,154 S | | 7/2007 | Lee |
| D564,662 S | | 3/2008 | Moses et al. |
| D567,943 S | | 4/2008 | Moses et al. |
| D575,395 S | | 8/2008 | Hushka |
| D575,401 S | | 8/2008 | Hixson et al. |
| D582,038 S | | 12/2008 | Swoyer et al. |
| 7,628,791 B2 | * | 12/2009 | Garrison ............ A61B 18/1445 |
| | | | 606/51 |
| D617,900 S | | 6/2010 | Kingsley et al. |
| D617,901 S | | 6/2010 | Unger et al. |
| D617,902 S | | 6/2010 | Twomey et al. |
| D617,903 S | | 6/2010 | Unger et al. |
| D618,798 S | | 6/2010 | Olson et al. |
| D621,503 S | | 8/2010 | Otten et al. |
| D627,462 S | | 11/2010 | Kingsley |
| D628,289 S | | 11/2010 | Romero |
| D628,290 S | | 11/2010 | Romero |
| D630,324 S | | 1/2011 | Reschke |
| 7,922,718 B2 | | 4/2011 | Moses et al. |
| D649,249 S | | 11/2011 | Guerra |
| D649,643 S | | 11/2011 | Allen, IV et al. |
| 8,152,806 B2 | | 4/2012 | Black et al. |
| D661,394 S | | 6/2012 | Romero et al. |
| 8,496,682 B2 | * | 7/2013 | Guerra ............... A61B 18/1445 |
| | | | 606/205 |
| 8,545,534 B2 | * | 10/2013 | Ahlberg ............... A61B 17/282 |
| | | | 606/207 |
| 8,551,088 B2 | * | 10/2013 | Falkenstein ........ A61B 18/1206 |
| | | | 606/51 |
| 8,679,140 B2 | | 3/2014 | Butcher |
| RE44,834 E | | 4/2014 | Dumbauld et al. |
| 8,939,973 B2 | | 1/2015 | Garrison et al. |
| 8,945,126 B2 | | 2/2015 | Garrison et al. |
| 8,945,127 B2 | | 2/2015 | Garrison et al. |
| 9,113,907 B2 | | 8/2015 | Allen, IV et al. |
| 9,113,937 B2 | | 8/2015 | Collings et al. |
| 9,119,630 B2 | | 9/2015 | Townsend et al. |
| 9,124,013 B2 | | 9/2015 | Frushhour et al. |
| 9,161,769 B2 | | 10/2015 | Stoddard et al. |
| 9,192,421 B2 | | 11/2015 | Garrison |
| 9,241,732 B2 | | 1/2016 | Craig |
| 9,259,266 B2 | | 2/2016 | Schmaltz et al. |
| 9,265,566 B2 | | 2/2016 | O'Neill et al. |
| 9,368,004 B2 | | 6/2016 | Plaven |
| 9,375,205 B2 | | 6/2016 | Mueller |
| 9,375,227 B2 | | 6/2016 | Garrison et al. |
| 9,375,256 B2 | | 6/2016 | Cunningham et al. |
| 9,375,259 B2 | | 6/2016 | Payne et al. |
| 9,375,260 B2 | | 6/2016 | Kerr |
| 9,375,262 B2 | | 6/2016 | Reschke et al. |
| 9,433,461 B2 | | 9/2016 | Arya et al. |
| 9,456,863 B2 | | 10/2016 | Moua |
| 9,480,522 B2 | | 11/2016 | Horner et al. |
| 9,498,281 B2 | | 11/2016 | Kendrick |
| 9,526,564 B2 | | 12/2016 | Rusin |
| 9,549,749 B2 | | 1/2017 | Kendrick |
| 9,572,529 B2 | | 2/2017 | Latimer et al. |
| 9,636,168 B2 | | 5/2017 | Payne et al. |
| 9,681,908 B2 | | 6/2017 | Garrison |
| 9,713,491 B2 | | 7/2017 | Roy et al. |
| 9,839,467 B2 | | 12/2017 | Harper et al. |
| 9,877,775 B2 | | 1/2018 | Hart |
| 10,070,916 B2 | * | 9/2018 | Artale ............... A61B 18/1445 |
| 2002/0188294 A1 | | 12/2002 | Couture et al. |
| 2003/0018331 A1 | | 1/2003 | Dycus et al. |
| 2003/0109875 A1 | | 6/2003 | Tetzlaff et al. |
| 2003/0171747 A1 | | 9/2003 | Kanehira et al. |
| 2003/0229344 A1 | | 12/2003 | Dycus et al. |

(56) References Cited

U.S. PATENT DOCUMENTS

| | | | |
|---|---|---|---|
| 2004/0176762 | A1 | 9/2004 | Lawes et al. |
| 2004/0243125 | A1* | 12/2004 | Dycus ............... A61B 18/1445 606/51 |
| 2005/0154387 | A1 | 7/2005 | Moses et al. |
| 2007/0260241 | A1 | 11/2007 | Dalla Betta et al. |
| 2008/0114349 | A1 | 5/2008 | Treat |
| 2008/0215048 | A1 | 9/2008 | Hafner et al. |
| 2008/0262491 | A1 | 10/2008 | Swoyer et al. |
| 2010/0030205 | A1 | 2/2010 | Herzon |
| 2010/0179540 | A1 | 7/2010 | Marczyk et al. |
| 2011/0184459 | A1 | 7/2011 | Malkowski et al. |
| 2011/0190765 | A1 | 8/2011 | Chojin |
| 2011/0251613 | A1 | 10/2011 | Guerra et al. |
| 2011/0301592 | A1 | 12/2011 | Kerr et al. |
| 2012/0022524 | A1 | 1/2012 | Timm et al. |
| 2012/0022529 | A1 | 1/2012 | Shelton, IV et al. |
| 2012/0136347 | A1 | 5/2012 | Brustad et al. |
| 2012/0172868 | A1* | 7/2012 | Twomey ............. A61B 18/1445 606/41 |
| 2013/0018411 | A1 | 1/2013 | Collings et al. |
| 2013/0296848 | A1* | 11/2013 | Allen, IV .......... A61B 18/1445 606/41 |
| 2013/0296922 | A1* | 11/2013 | Allen, IV ............ A61B 17/282 606/205 |
| 2014/0066910 | A1 | 3/2014 | Nau, Jr. |
| 2014/0066911 | A1 | 3/2014 | Nau, Jr. |
| 2014/0094798 | A1 | 4/2014 | Garrison et al. |
| 2014/0100564 | A1 | 4/2014 | Garrison |
| 2014/0100569 | A1 | 4/2014 | Lawes et al. |
| 2014/0107443 | A1 | 4/2014 | Hoarau et al. |
| 2014/0121507 | A1 | 5/2014 | Nau, Jr. |
| 2014/0135763 | A1 | 5/2014 | Kappus et al. |
| 2014/0194875 | A1 | 7/2014 | Reschke et al. |
| 2014/0221994 | A1 | 8/2014 | Reschke |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009318 U1 | 8/2007 |
| DE | 202007009317 U1 | 10/2007 |
| DE | 202007016233 U1 | 1/2008 |
| DE | 102008018406 B3 | 7/2009 |
| EP | 1281878 A1 | 2/2003 |
| EP | 1159926 A2 | 3/2003 |
| EP | 1645238 A1 | 4/2006 |
| EP | 1810625 A1 | 7/2007 |
| EP | 2347725 A1 | 7/2011 |
| EP | 2436330 A1 | 4/2012 |
| EP | 2659848 A2 | 11/2013 |
| EP | 2659849 A3 | 1/2014 |
| JP | 61501068 | 9/1984 |
| JP | 6502328 | 3/1992 |
| JP | 55106 | 1/1993 |
| JP | 0540112 | 2/1993 |
| JP | 6121797 | 5/1994 |
| JP | 6285078 | 10/1994 |
| JP | 06343644 A | 12/1994 |
| JP | 6511401 | 12/1994 |
| JP | 07265328 A | 10/1995 |
| JP | 856955 | 3/1996 |
| JP | 08252263 A | 10/1996 |
| JP | 8289895 | 11/1996 |
| JP | 8317934 | 12/1996 |
| JP | 8317936 | 12/1996 |
| JP | 910223 | 1/1997 |
| JP | 09000538 A | 1/1997 |
| JP | 9122138 | 5/1997 |
| JP | 1024051 | 1/1998 |
| JP | 0010000195 A | 1/1998 |
| JP | 10155798 | 6/1998 |
| JP | 1147150 | 2/1999 |
| JP | 11047149 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A2 | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 0006030945 B2 | 11/2016 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 02080799 A1 | 10/2002 |
| WO | 2006021269 A1 | 3/2006 |
| WO | 2005110264 A2 | 4/2006 |
| WO | 2008040483 A1 | 4/2008 |
| WO | 2008045348 A2 | 4/2008 |
| WO | 2011018154 A1 | 2/2011 |
| WO | 2011044343 A2 | 4/2011 |

OTHER PUBLICATIONS

Extended European Search Report from Application No. 14158819.4 dated Jun. 10, 2014.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Schmaltz et al.
U.S. Appl. No. 09/591,328, filed Jun. 9, 2000, Ryan et al.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small,

(56) References Cited

OTHER PUBLICATIONS

Medium, and Large-Sized Arteries" Carolinas Laparoscopic and Advanced Surgery Program, Carolinas Medical Center,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview", Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties At VHF Through Microwave Frequencies", IEEE Transactions on Microwave Theory and Techniques vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer"; Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al."Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy"; FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.

\* cited by examiner

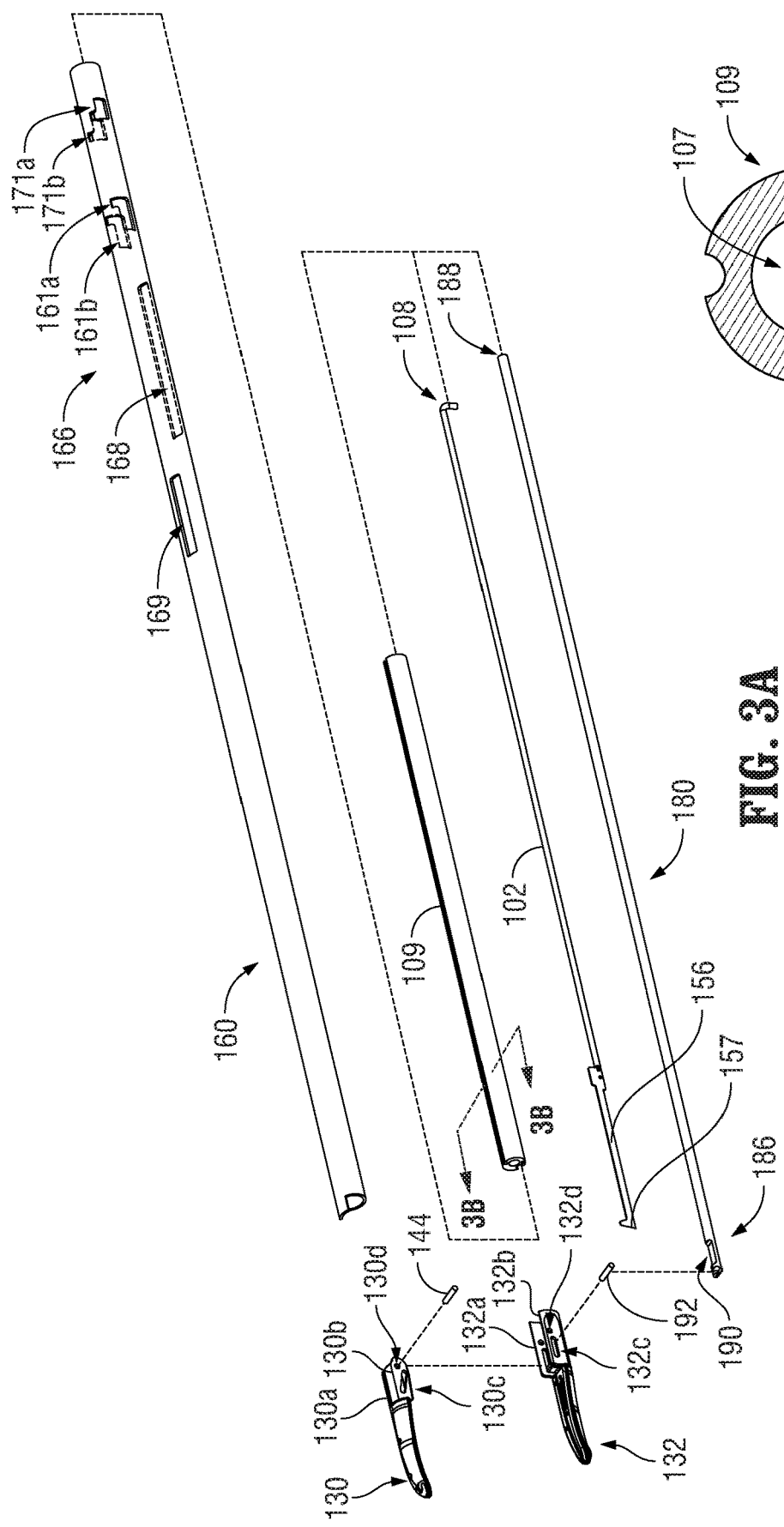
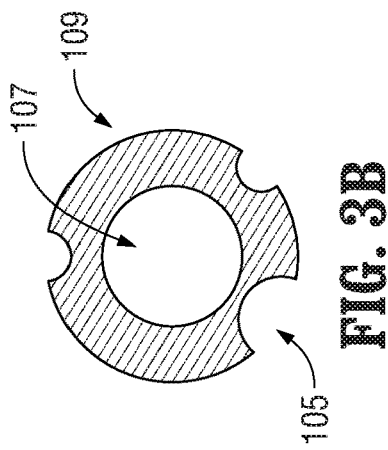

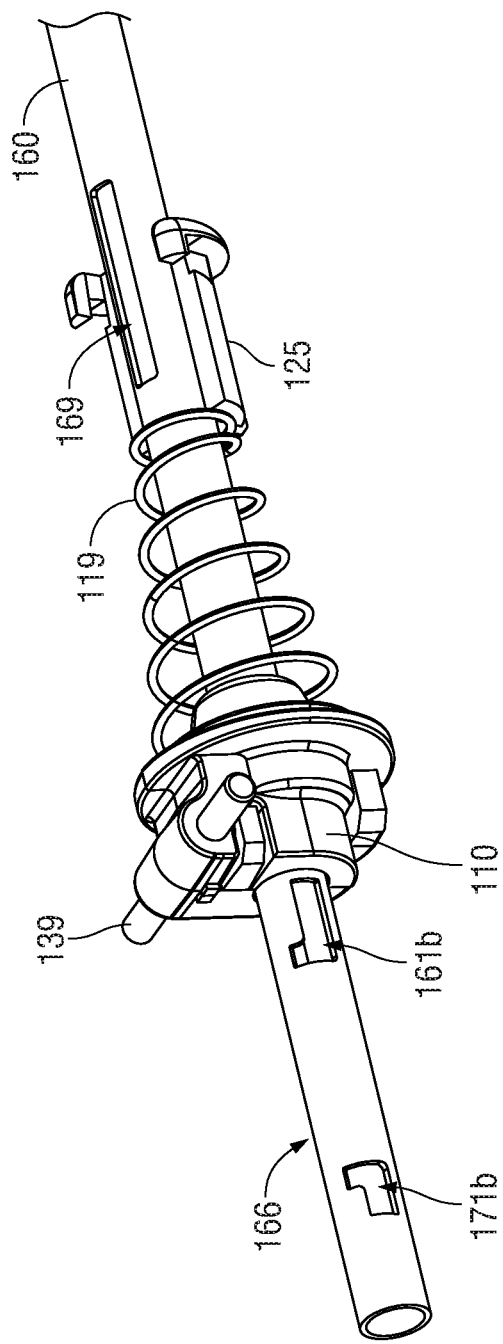
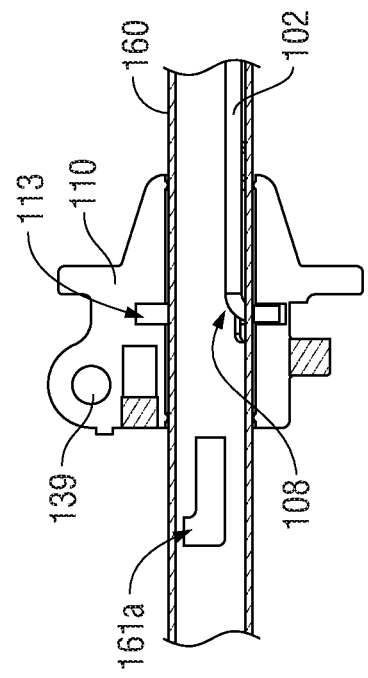
FIG. 12A
FIG. 12B

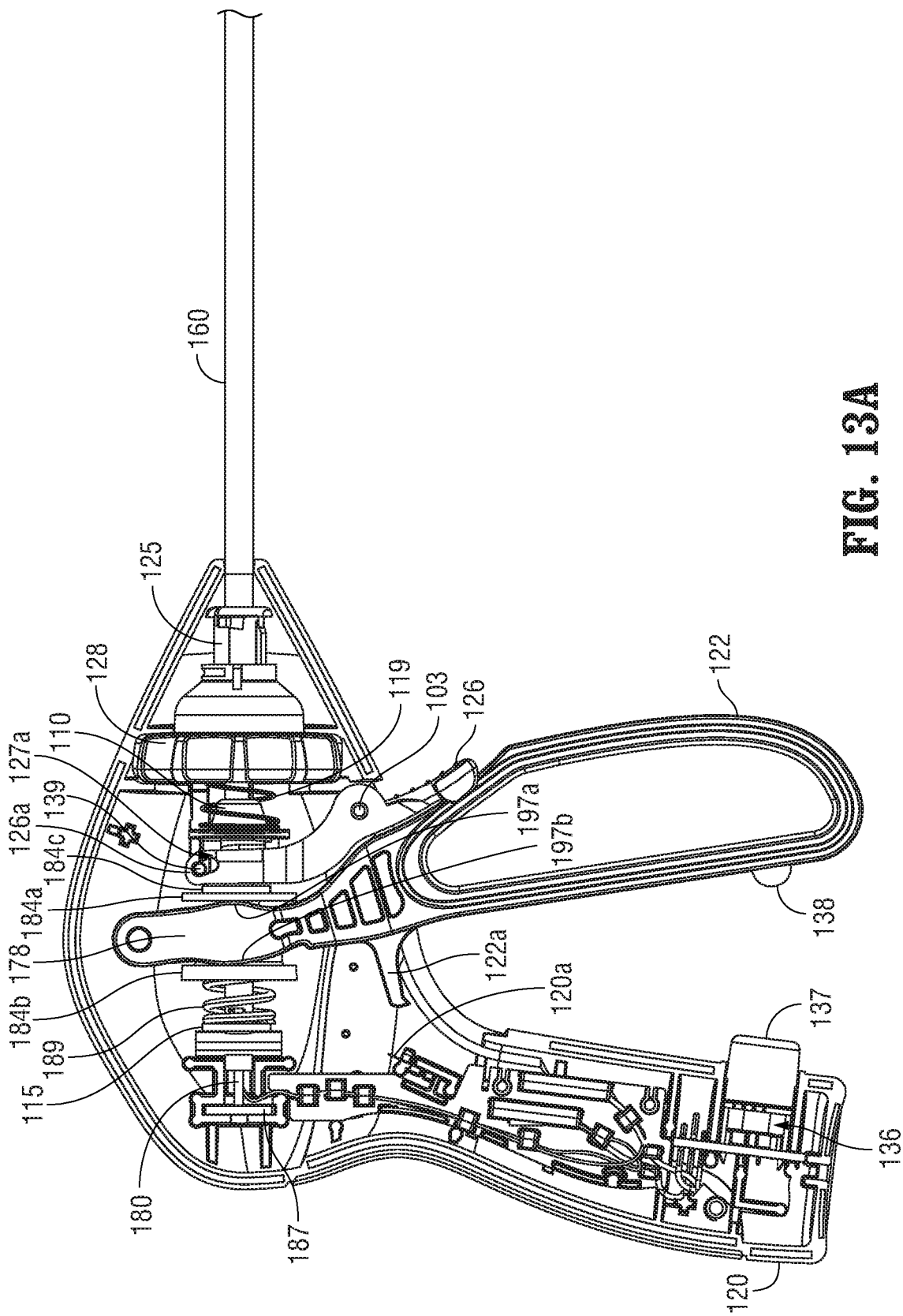

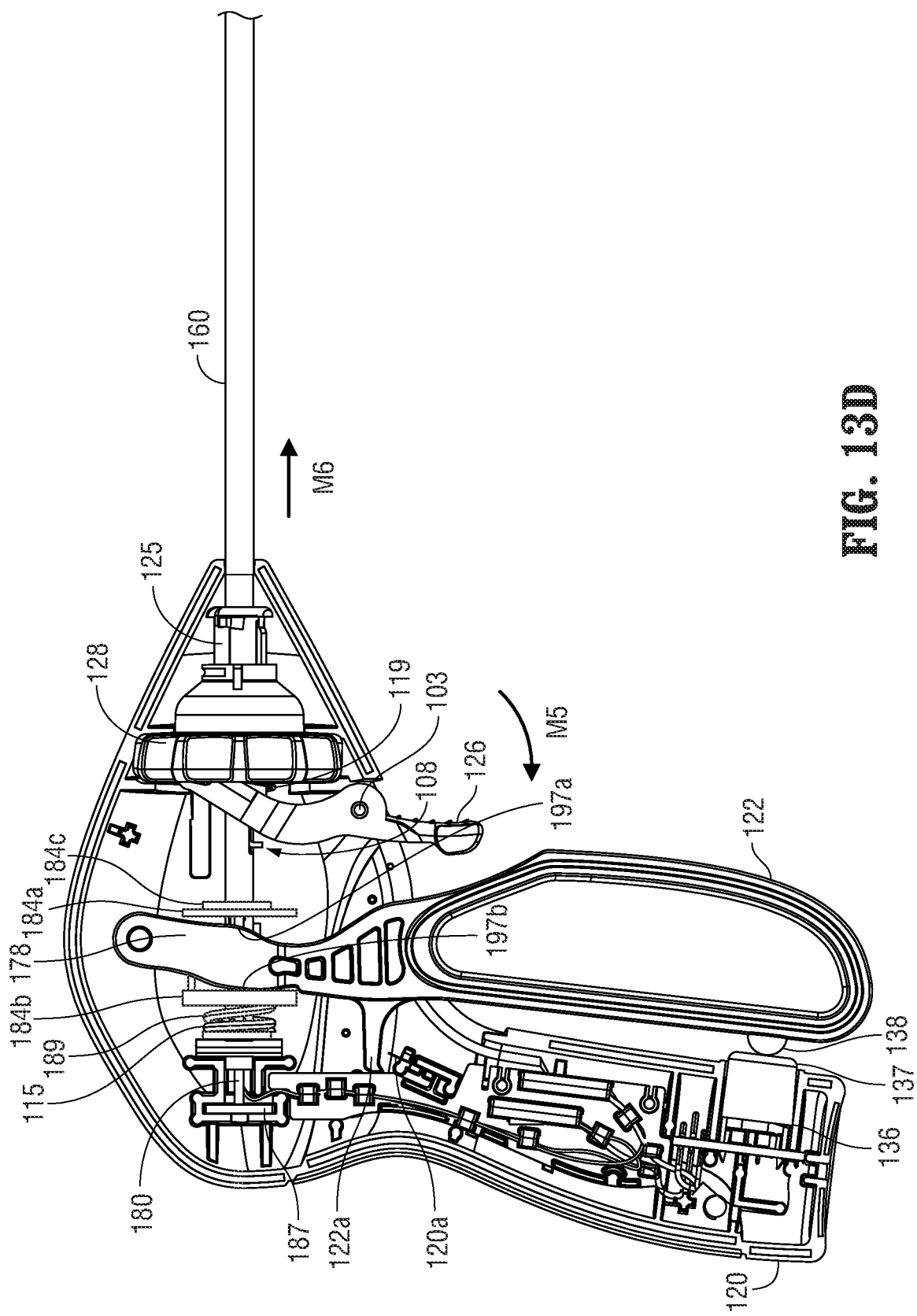

SURGICAL INSTRUMENT WITH SYSTEM AND METHOD FOR SPRINGING OPEN JAW MEMBERS

CROSS-REFERENCE TO RELATED APPLICATIONS

The present application is a continuation of U.S. patent application Ser. No. 14/152,618 filed on Jan. 10, 2014, which claims priority to U.S. Provisional Application No. 61/776,159, filed on Mar. 11, 2013, the entire contents of each of which are incorporated herein by reference.

BACKGROUND

Technical Field

The present disclosure relates generally to the field of surgical instruments. In particular, the disclosure relates to an endoscopic electrosurgical forceps that includes a system and method for springing open jaw members.

Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 kg/cm2 to about 16 kg/cm$^2$.

SUMMARY

The present disclosure relates generally to the field of surgical instruments. In particular, the disclosure relates to an endoscopic electrosurgical forceps that includes a system and method for springing open jaw members.

As is traditional, the term "distal" refers herein to an end of the apparatus that is farther from an operator, and the term "proximal" refers herein to the end of the electrosurgical forceps that is closer to the operator.

According to an aspect of the present disclosure, a surgical instrument is provided. The surgical instrument includes a housing and an elongated shaft. The elongated shaft has a distal portion extending therefrom and a proximal portion coupled to the housing. A longitudinal axis is defined through the elongated shaft. A stationary actuation member is axially disposed within the elongated shaft and includes a cam pin mechanically coupled to the distal portion of the elongated shaft. An actuating mechanism is operably coupled to the proximal portion of the elongated shaft and is moveable relative to the housing between an actuated position and an unactuated position to selectively move the elongated shaft along the longitudinal axis relative to the stationary actuation member. An end effector includes a pair of opposing first and second jaw members operably coupled about a common pivot such that one or both of the jaw members is movable relative to the other jaw member from a first position wherein the jaw members are disposed in spaced relation relative to one another to a second position wherein the jaw members cooperate to grasp tissue. One or both of the first and second jaw members includes a camming slot configured to engage the cam pin to move the one or more movable jaw members between the first position and the second position upon movement of the elongated shaft along the longitudinal axis. One or both drive surfaces is disposed on the actuating mechanism and is configured to compress a spring upon movement of the actuating mechanism to the actuated position. The spring imparts a spring force in a distal direction to bias the actuating mechanism to the unactuated position. An electrically conductive tissue sealing surface extends along a length of one or both jaw members. The tissue sealing surface is adapted to connect to a source of electrosurgical energy for conducting electrosurgical energy through tissue disposed between the jaw members to effect a tissue seal. A knife blade is supported in the elongated shaft and is moveable in a longitudinal direction through a knife channel defined along a length of one or both of the jaw members to cut tissue disposed between the jaw members.

Additionally or alternatively, the surgical instrument may also include a switch supported by the housing and configured to be engaged by the actuating mechanism to initiate delivery of electrosurgical energy from the electrosurgical energy source to the end effector to treat tissue.

Additionally or alternatively, the switch may be operably coupled to a depressible button extending from the housing and configured to be selectively engaged by the actuating mechanism.

Additionally or alternatively, the switch may be a two-stage switch or a multi-stage switch.

Additionally or alternatively, the surgical instrument may also include a drive collar operably coupled to the actuating mechanism and moveable along the longitudinal axis in response to movement of the actuating mechanism. The drive collar may be configured to compress the spring upon movement of the actuating mechanism to the actuated position.

Additionally or alternatively, the spring may be disposed between a proximal stop operably coupled to the proximal portion of the elongated shaft and a proximal end of the drive collar.

Additionally or alternatively, the spring imparts a spring force on the proximal end of the drive collar in a distal direction to bias the actuating mechanism to the unactuated position.

Additionally or alternatively, the second jaw member may be mechanically coupled to a distal end of the elongated shaft and the first jaw member may be configured to move relative to the second jaw member.

Additionally or alternatively, the actuating mechanism may include a handle moveable relative to the housing between a distal position to move the at least one jaw member to the first position and a proximal position to move the at least one jaw member to the second position.

Additionally or alternatively, the handle may engage the switch upon movement thereof to the proximal position.

According to another aspect of the present disclosure, a surgical instrument is provided. The surgical instrument includes a housing and an elongated shaft having a distal portion extending from the housing and a proximal portion coupled to the housing. A longitudinal axis is defined through the elongated shaft. A stationary actuation member is axially disposed within the elongated shaft and includes a cam pin mechanically coupled to the distal portion of the elongated shaft. An actuating mechanism is operably coupled to the proximal portion of the elongated shaft and is moveable relative to the housing between an actuated position and an unactuated position to selectively move the elongated shaft along the longitudinal axis relative to the stationary actuation member. An end effector includes a pair of opposing first and second jaw members operably coupled about a common pivot such one or both of the jaw members is movable relative to the other jaw member from a first position wherein the jaw members are disposed in spaced relation relative to one another to a second position wherein the jaw members cooperate to grasp tissue between the jaw members. One or both of the first and second jaw members includes a camming slot configured to engage the cam pin to move the one or more movable jaw members between the first position and the second position upon movement of the elongated shaft along the longitudinal axis. A drive collar is operably coupled to the actuating mechanism and is moveable along the longitudinal axis in response to movement of the actuating mechanism. The drive collar is configured to compress a spring upon movement of the actuating mechanism to the actuated position. The spring imparts a spring force on the drive collar in a distal direction to bias the actuating mechanism to the unactuated position. An electrically conductive tissue sealing surface extends along a length of one or both jaw members. The tissue sealing surface is adapted to connect to a source of electrosurgical energy for conducting electrosurgical energy through tissue grasped between the jaw members to effect a tissue seal. A knife blade is supported in the elongated shaft and is moveable in a longitudinal direction through a knife channel defined along a length of one or both of the jaw members to cut tissue disposed between the jaw members.

Additionally or alternatively, the spring may be disposed between a proximal stop operably coupled to the proximal portion of the elongated shaft and a proximal end of the drive collar.

Additionally or alternatively, the spring may impart a spring force on a proximal end of the drive collar in a distal direction to bias the actuating mechanism to the unactuated position.

Additionally or alternatively, the actuating mechanism includes one or more drive surfaces operably coupled to the drive collar configured to engage a proximal rim of the drive collar upon movement of the actuating mechanism to move the drive collar along the longitudinal axis.

According to another aspect of the present disclosure, an electrosurgical system for performing electrosurgery is provided. The system include an electrosurgical generator configured to provide electrosurgical energy and an electrosurgical instrument. The surgical instrument includes a housing and an elongated shaft. The elongated shaft has a distal portion extending therefrom and a proximal portion coupled to the housing. A longitudinal axis is defined through the elongated shaft. A stationary actuation member is axially disposed within the elongated shaft and includes a cam pin mechanically coupled to the distal portion of the elongated shaft. An actuating mechanism is operably coupled to the proximal portion of the elongated shaft and is moveable relative to the housing between an actuated position and an unactuated position to selectively move the elongated shaft along the longitudinal axis relative to the stationary actuation member. An end effector includes a pair of opposing first and second jaw members operably coupled about a common pivot such that one or both of the jaw members is movable relative to the other jaw member from a first position wherein the jaw members are disposed in spaced relation relative to one another to a second position wherein the jaw members cooperate to grasp tissue. One or both of the first and second jaw members includes a camming slot configured to engage the cam pin to move the one or more movable jaw members between the first position and the second position upon movement of the elongated shaft along the longitudinal axis. One or both drive surfaces is disposed on the actuating mechanism and is configured to compress a spring upon movement of the actuating mechanism to the actuated position. The spring imparts a spring force in a distal direction to bias the actuating mechanism to the unactuated position. An electrically conductive tissue sealing surface extends along a length of one or both jaw members. The tissue sealing surface is adapted to connect to a source of electrosurgical energy for conducting electrosurgical energy through tissue disposed between the jaw members to effect a tissue seal. A knife blade is supported in the elongated shaft and is moveable in a longitudinal direction through a knife channel defined along a length of one or both of the jaw members to cut tissue disposed between the jaw members. A switch is supported by the housing and is configured to be engaged by the actuating mechanism to initiate delivery of electrosurgical energy from the electrosurgical energy source to the end effector to treat tissue.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 3A is a perspective view of the end effector and elongated shaft of FIG. 1 with parts separated;

FIG. 3B is cross-sectional view taken along line 3B-3B of FIG. 3A showing a distal portion of the electrosurgical forceps of FIG. 1 depicting a tube guide;

FIG. 12A is an enlarged, perspective view of a proximal portion of the knife actuation mechanism of the end effector of FIG. 1;

FIG. 12B is an enlarged, cross-sectional, side view of a knife collar of the knife actuation mechanism of the end effector of FIG. 1;

FIG. 13A is an internal, side view of the proximal portion of the instrument of FIG. 10 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members;

FIG. 13D is an internal, side view of the proximal portion of the instrument of FIG. 10 depicting the knife trigger in an actuated configuration, which corresponds to an actuated or distal position of the knife with respect to the jaw members.

DETAILED DESCRIPTION

Figure 1:
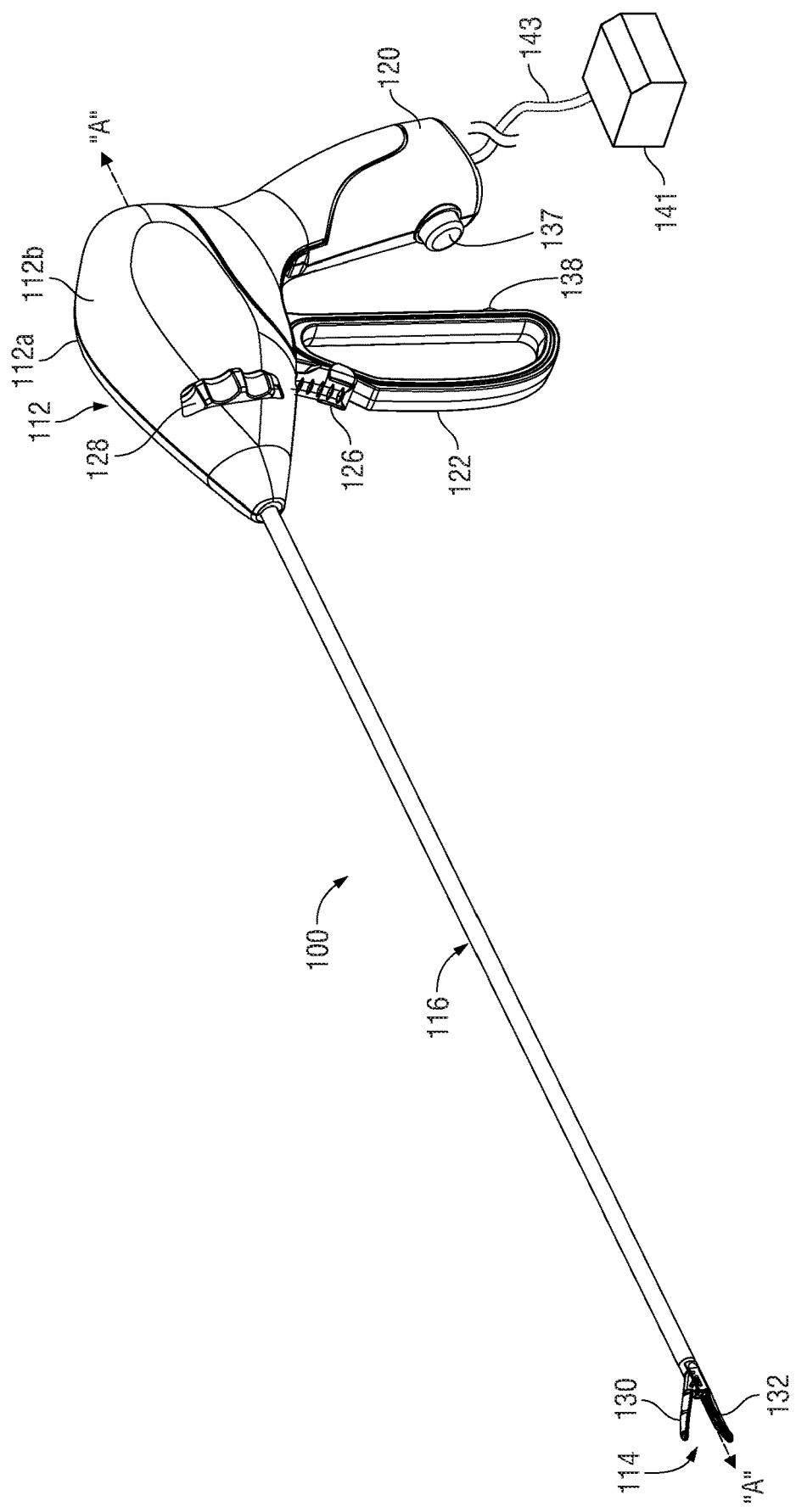
FIG. 1 is a perspective view of an electrosurgical forceps according to an embodiment of the present disclosure including a housing, an elongated shaft, and an end effector.

Referring initially to FIG. 1, an embodiment of an electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with certain endoluminal procedures.

The housing 112 is constructed of a left housing half 112a and a right housing half 112b. The left and right designation of the housing halves 112a, 112b refer to the respective directions as perceived by an operator using the forceps 100. The housing halves 112a, 112b are constructed of sturdy plastic, and are joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration (FIG. 2A) wherein a pair of opposed jaw members 130, 132 are disposed in spaced relation relative to one another, and a closed or clamping configuration (FIG. 2B) wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. In some embodiments, the moveable handle 122 may be shaped to facilitate spring-biased separation of the moveable handle 122 from the stationary handle 120 to move the end effector 114 from the closed configuration to the open configuration, as discussed in detail hereinbelow.

The trigger 126 is operable to extend and retract a knife blade 156 (see FIGS. 2A and 2B) through the end effector 114 when the end effector 114 is in the closed configuration. The rotation knob 128 serves to rotate the elongated shaft 116 and the end effector 114 about a longitudinal axis A-A extending through the forceps.

Figure 13B:
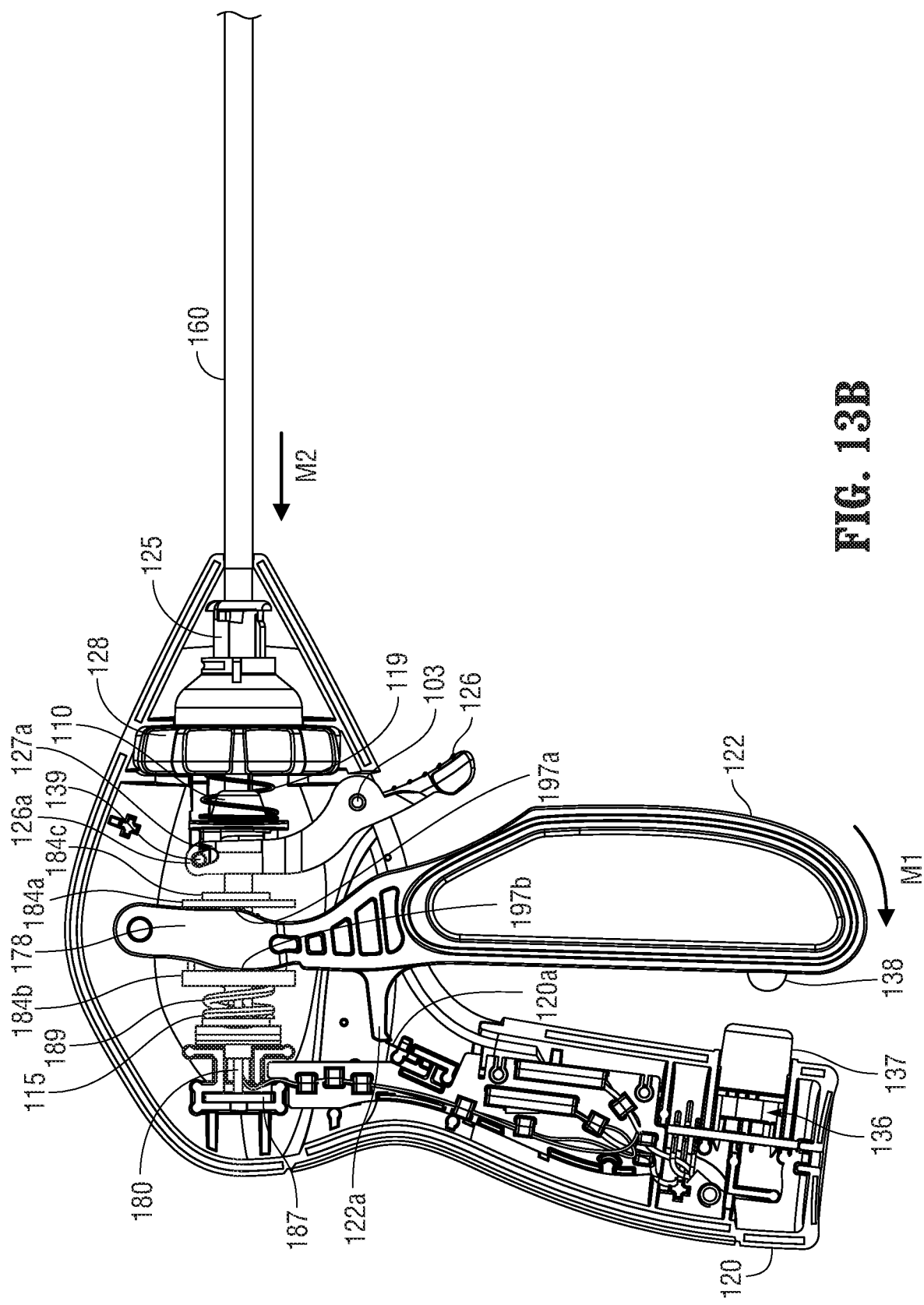
FIG. 13B is an internal, side view of the proximal portion of the instrument of FIG. 10 depicting the movable handle in an intermediate position with respect to the stationary handle, which corresponds to a first closed configuration of the end effector wherein the jaw members encounter one another.
Figure 13C:
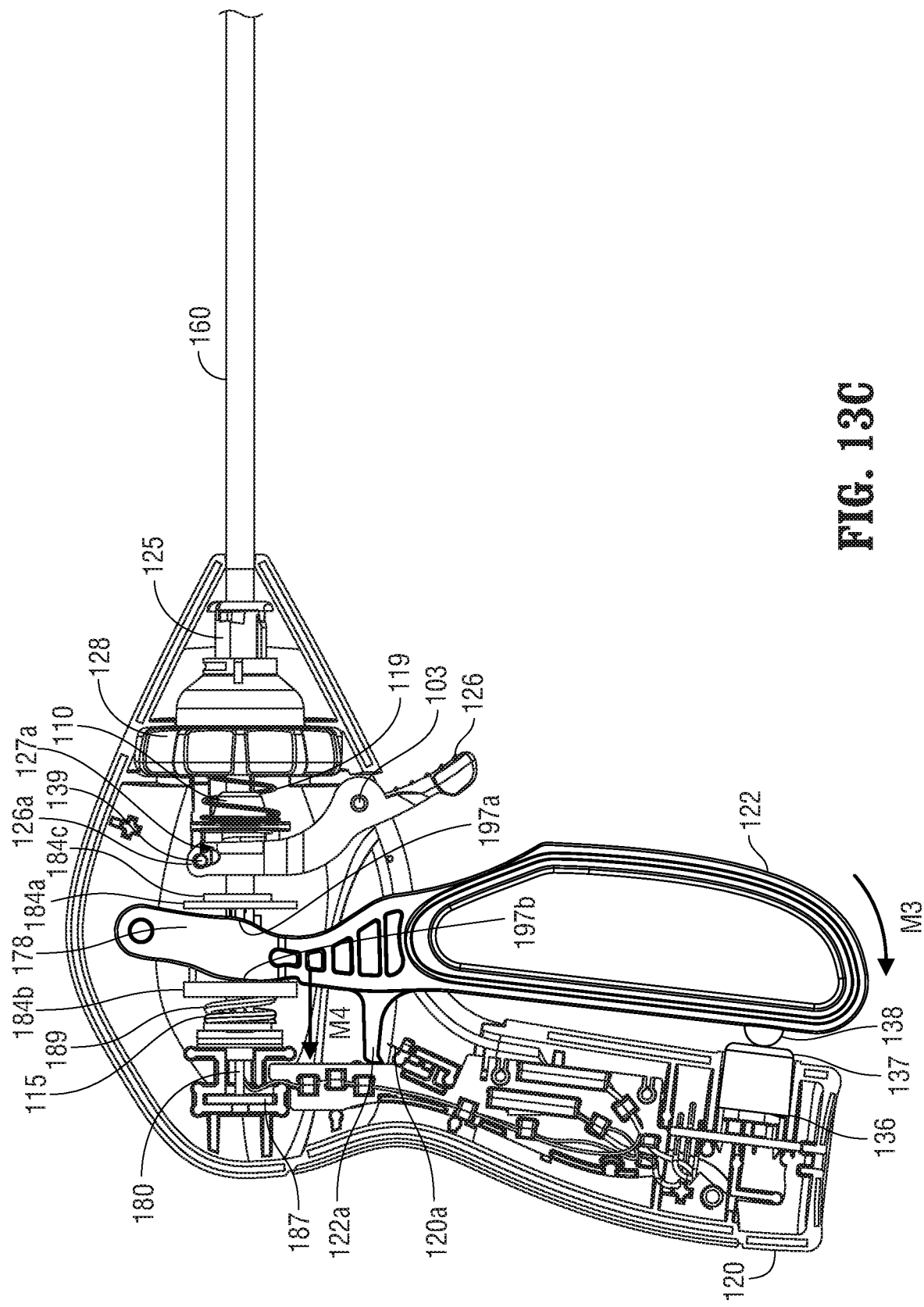
FIG. 13C is an internal, side view of the proximal portion of the instrument of FIG. 10 depicting the movable handle in an approximated configuration with respect to the stationary handle, which corresponds to a second closed configuration of the end effector wherein the jaw members apply an appropriate pressure to generate a tissue seal.

To electrically control the end effector 114, the stationary handle 120 supports a depressible button 137 thereon, which is operable by the user to initiate and terminate the delivery of electrosurgical energy to the end effector 114. More specifically, and as illustrated in FIGS. 13A-13D, the depressible button 137 is mechanically coupled to a switch 136 disposed within the stationary handle 120 and is engageable by a button activation post 138 extending from a proximal side of the moveable handle 122 upon proximal movement of the moveable handle 122 to an actuated or proximal position as depicted in FIG. 13C. The switch 136 is in electrical communication with a source of electrosurgical energy such as electrosurgical generator 141 or a battery (not shown) supported within the housing 112. The generator 141 may include devices such as the LIGA-SURE® Vessel Sealing Generator and the Force Triad® Generator sold by Covidien. A cable 143 extends between the housing 112 and the generator 141 and includes a connector (not shown) thereon such that the forceps 100 may be selectively coupled and decoupled electrically from the generator 141.

Figure 2A:
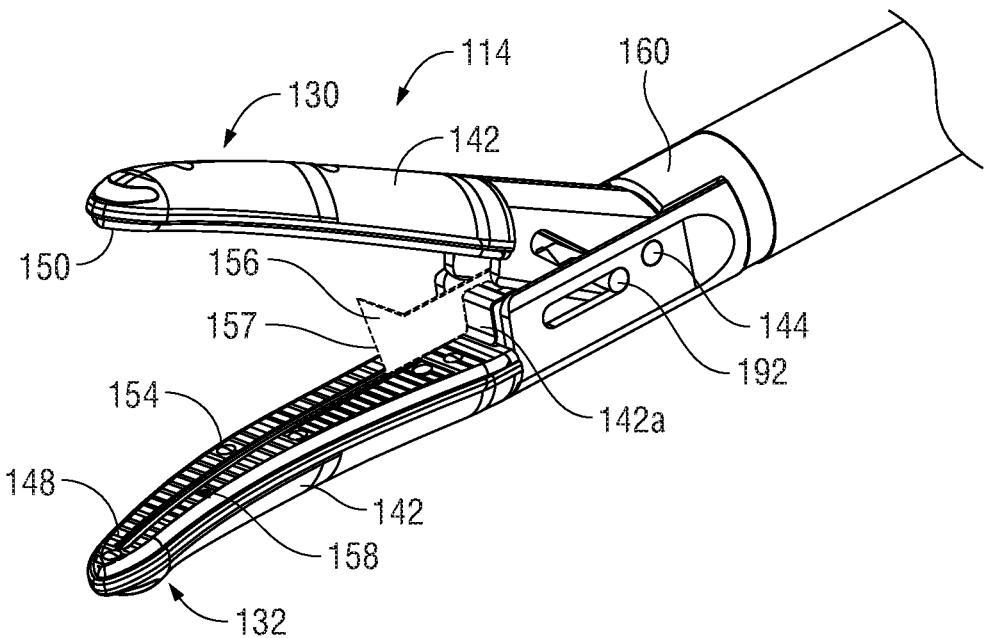
FIG. 2A is an enlarged, perspective view of the end effector of FIG. 1 depicted with a pair of jaw members in an open configuration.
Figure 2B:
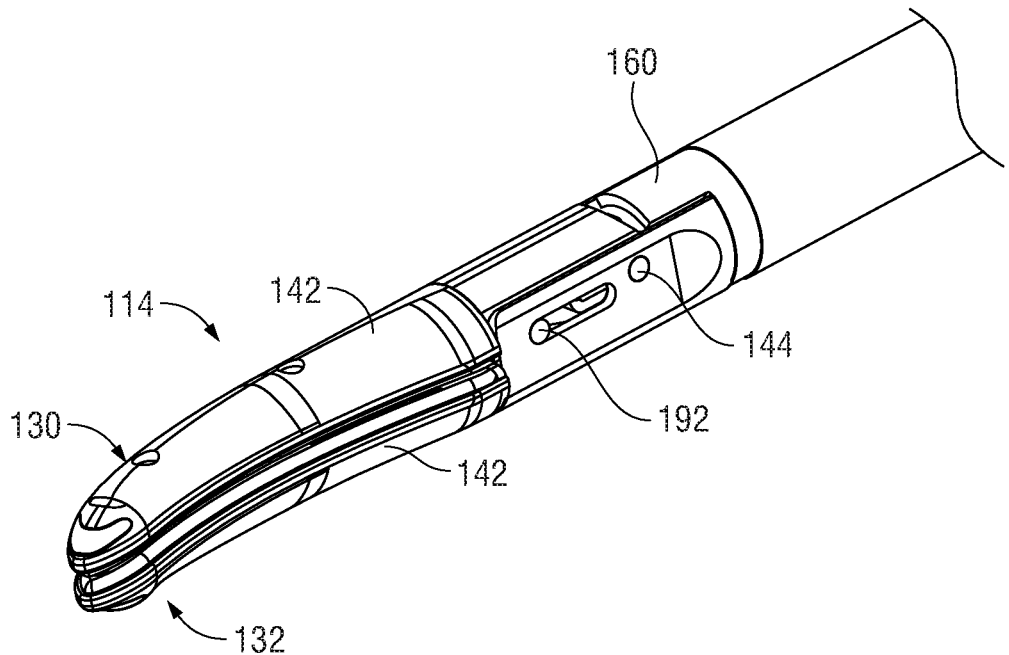
FIG. 2B is an enlarged, perspective view of the end effector of FIG. 1 depicted with the pair of jaw members in a closed configuration.

Referring now to FIGS. 2A-3, the end effector 114 may be moved from the open configuration (FIG. 2A) wherein tissue (not shown) is received between the jaw members 130, 132, and the closed configuration (FIG. 2B), wherein the tissue is clamped and sealed. The upper and lower jaw members 130, 132 are electrically coupled to cable 143, and thus to the generator 141 (e.g., via a respective wire extending through the elongated shaft 116) to provide an electrical pathway to a pair of electrically conductive, tissue-engaging sealing plates 148, 150 disposed on the lower and upper jaw members 132, 130, respectively. The sealing plate 148 of the lower jaw member 132 opposes the sealing plate 150 of the upper jaw member 130, and, in some embodiments, the sealing plates 148 and 150 are electrically coupled to opposite terminals, e.g., positive or active (+) and negative or return (−) terminals associated with the generator 141. Thus, bipolar energy may be provided through the sealing plates 148 and 150. Alternatively, the sealing plates 148 and 150 and/or the end effector 114 may be configured for delivering monopolar energy to the tissue. In a monopolar configuration, one or both sealing plates 148 and 150 deliver electrosurgical energy from an active terminal, e.g. (+), while a return pad (not shown) is placed generally on a patient and provides a return path to the opposite terminal, e.g. (−), of the generator 141. Each jaw member 130, 132 includes a jaw insert 140 and an insulator 142 that serves to electrically insulate the sealing plates 150, 148 from the jaw insert 140 of jaw members 130, 132, respectively.

Figure 10:
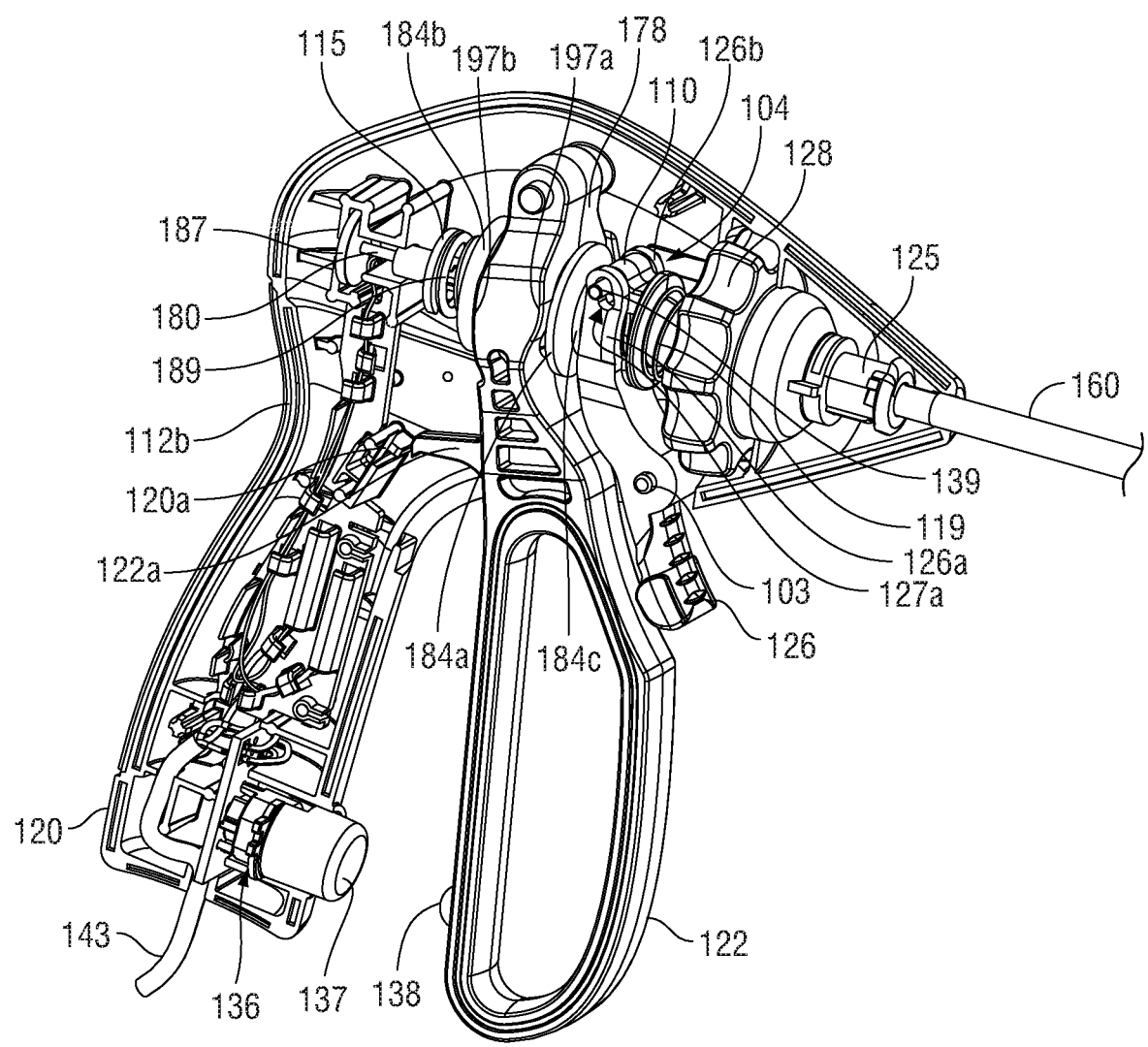
FIG. 10 is a perspective view of a proximal portion of the instrument of FIG. 1 with a portion of the housing removed revealing internal components.

Referring to FIG. 3, the elongated shaft 116 includes various longitudinal components that operatively couple the end effector 114 to the various actuators supported by the housing 112 (FIG. 1). An outer shaft member 160 defines an exterior surface of the elongated shaft 116 and supports movement of other components therethrough as described below. The outer shaft member 160 is configured for longitudinal motion with respect to an inner actuation member 180 axially received within the outer shaft member 160. The inner actuation member 180 may be a rod, shaft, stamped metal, or other suitable mechanical component. A proximal portion 166 of the outer shaft member 160 is configured for receipt within the housing 112 (FIG. 1), and includes features for operatively coupling the outer shaft member 160 to the actuators supported thereon, e.g. the movable handle 122. A distal portion 186 of the inner actuation member 180 includes a longitudinal recess 190 defined therein that provides clearance for the pivot pin 144 and thus, permits longitudinal reciprocation of the pivot pin 144 (via longitudinal reciprocation of the outer shaft member 160) independent of the inner actuation member 180. Distally of the longitudinal recess 190, the cam pin 192 is mechanically coupled (e.g., via welding, friction-fit, laser welding, etc.) to the distal portion 186 of the inner actuation member 180. A proximal portion 188 of the inner actuation member 180 includes a washer 187 coupled thereto (FIG. 10). The washer 187 is supported within the housing 112 and serves to prohibit longitudinal motion of the inner actuation member 180 along the longitudinal axis A-A.

The jaw members 130, 132 may be pivoted about the pivot pin 144 to move the end effector 114 to the closed configuration of FIG. 2B wherein the sealing plates 148, 150 provide a pressure to tissue grasped therebetween. In some embodiments, to provide an effective seal, a pressure within a range between about 3 kg/cm2 to about 16 kg/cm2 and, desirably, within a working range of 7 kg/cm2 to 13 kg/cm2 is applied to the tissue. Also, in the closed configuration, a separation or gap distance "G" may be maintained between the sealing plates 148, 150 by an array of stop members 154 (FIG. 2A) disposed on or adjacent the sealing plates 148, 150. The stop members 154 contact opposing surfaces on the opposing jaw member 130, 132 and prohibit further approximation of the sealing plates 148, 150. In some embodiments, to provide an effective tissue seal, an appropriate gap distance of about 0.001 inches to about 0.010 inches and, desirably, between about 0.002 and about 0.005 inches may be provided. In some embodiments, the stop members 154 are constructed of an electrically non-conductive plastic or other material molded onto the jaw members 130, 132, e.g., by a process such as overmolding or injection molding. In other embodiments, the stop members 154 are constructed of a heat-resistant ceramic deposited onto the jaw members 130, 132.

Electrosurgical energy may be delivered to the tissue through the electrically conductive seal plates 148, 150 to effect a tissue seal. Once a tissue seal is established, a knife blade 156 having a sharp distal cutting edge 157 may be advanced through a knife channel 158 defined in one or both jaw members 130, 132 to transect the sealed tissue. Knife blade 156 is depicted in FIG. 2A as extending from the elongated shaft 116 when the end effector 114 is in an open configuration. In some embodiments, a knife lockout is provided to prevent extension of the knife blade 156 into the knife channel 158 when the end effector 114 is in the open configuration.

The proximal portion 166 of the outer shaft member 160 includes various features that serve to couple the outer shaft member 160 to various elements of the housing 112. More specifically, the proximal portion 166 of the outer shaft member 160 includes, in order from distal to proximal, a longitudinal slot 169 extending distally from a proximal end thereof to couple the outer shaft member 160 to the rotation knob 128, a longitudinal knife slot 168 defined therethrough, a pair of opposing distal locking slots 161a, 161b, and a pair of opposing proximal locking slots 171a, 171b. The connection established between the outer shaft member 160 and the rotation knob 128 is described below with reference to FIG. 4.

Figures 8, 9:
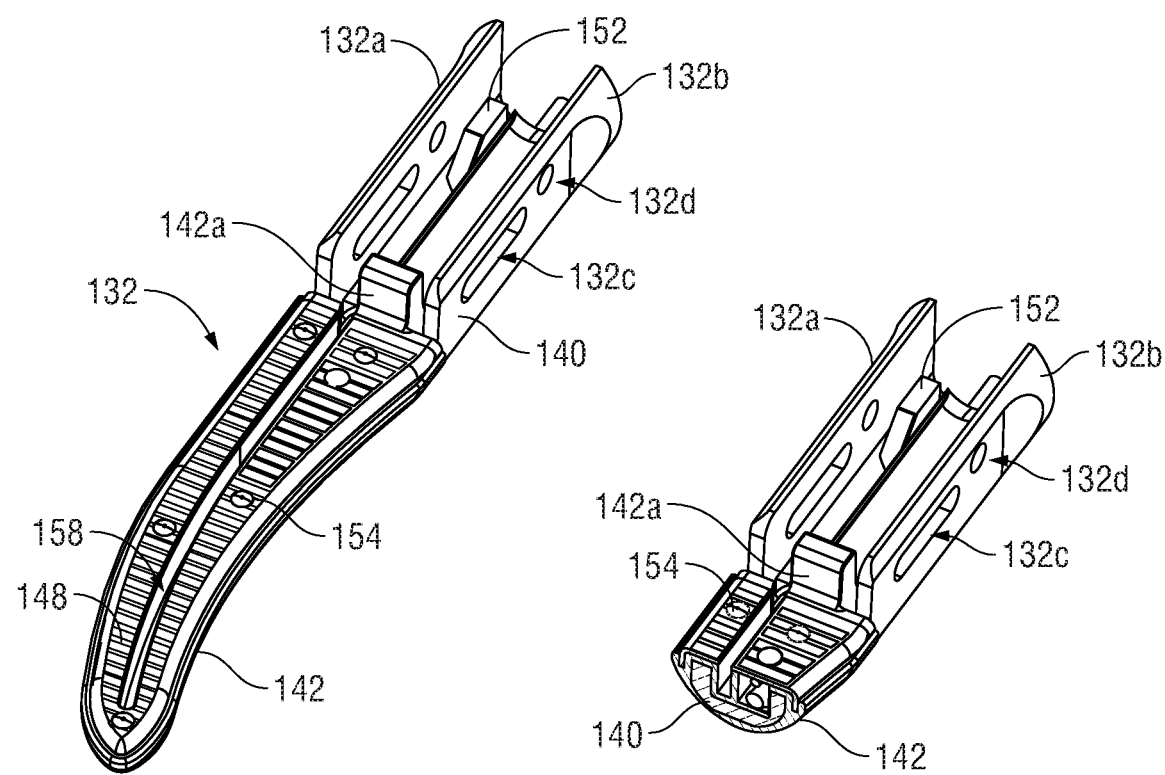
FIG. 8 is a top, perspective view of a lower jaw member of the end effector of FIG. 1.
FIG. 9 is a top, cross-sectional, perspective view of the lower jaw member of FIG. 8.

The pivot pin 144 extends through a proximal portion of each of the jaw members 130, 132 to pivotally support the jaw members 130, 132 at the distal end of the outer shaft member 160. With reference to FIG. 8, a proximal portion of each of the jaw members 130, 132 includes two laterally spaced parallel flanges or "flags" 130a, 130b and 132a, 132b respectively, extending proximally from a distal portion of the jaw members 130 and 132. A lateral cam slot 130c and a lateral pivot bore 130d extend through each of the flags 130a, 130b of the upper jaw member 130. Similarly, a lateral cam slot 132c and a lateral pivot bore 132d extend through each of the flags 132a, 132b of the lower jaw member 132. The pivot bores 130d, 132d receive the pivot pin 144 in a slip-fit relation that permits the jaw members 130, 132 to pivot about the pivot pin 144 to move the end effector 114 between the open and closed configurations (FIGS. 2A and 2B, respectively).

A knife rod 102 is coupled (e.g., via welding) at a distal-most end to the sharpened knife blade 156 and includes an angled proximal end 108 that provides a mechanism for operatively coupling the knife rod 102 to the trigger 126. The connection between the knife rod 102 and the trigger 126 is described in detail below with reference to FIGS. 10, 11, 12A, and 12B. The sharp edge 157 of the knife blade 156 may be applied to the distal end of the knife blade 156 subsequent to the stamping process that forms the profile. For example, various manufacturing techniques may be employed such as grinding, coining, electrochemical etching, electropolishing, or other suitable manufacturing processes, for forming sharpened edges.

A tube guide 109 is disposed within the outer shaft member 160 and includes a central guide lumen 107 axially disposed therethrough and a longitudinal guide recess 105 formed therein. The inner actuation member 180 is received within the central guide lumen 107, which serves to guide longitudinal motion of the inner actuation member 180 within the outer shaft member 160. The knife rod 102 is received within the longitudinal recess 105, which serves to guide longitudinal motion of the knife rod 102 within the outer shaft member 160. In this way, the inner actuation member 180 and the knife rod 102 are aligned within the outer shaft member 160 by the tube guide 109 such that the inner actuation member 180 and the knife rod 102 are free to move longitudinally relative to and in parallel with each other.

Figure 4:
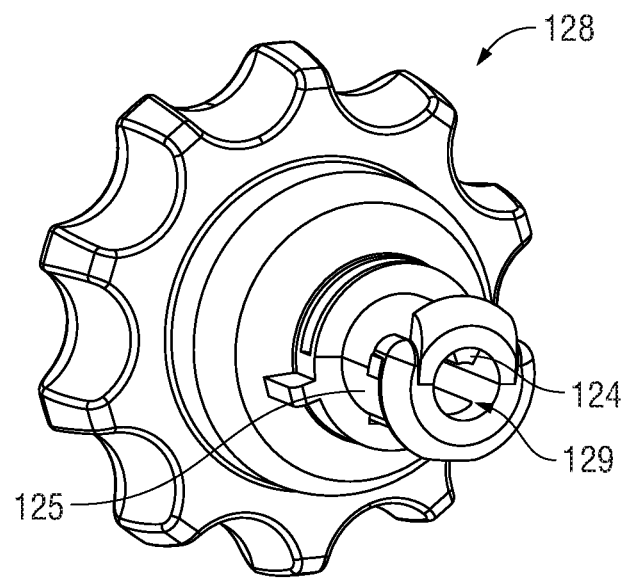
FIG. 4 is a proximally-facing, perspective view of a rotation knob depicting a passageway for receiving the elongated shaft of FIG. 1.

Referring now to FIG. 4, the rotation knob 128 includes a passageway 129 defined therethrough for receiving the outer shaft member 160. The passageway 129 has a generally circular profile corresponding to the circular profile of the outer shaft member 160. The passageway 129 includes a longitudinal keying member 124 that is configured to align with and be seated within longitudinal slot 169 (FIG. 3A) of the outer shaft member 160. The keying member 124 projects laterally inward along the length of passageway 129 such that the insertion of the proximal end of the outer shaft member 160 into the passageway 129 of the rotation knob 128 operatively couples the outer shaft member 160 to the rotation knob 128 and, thus, permits longitudinal motion of the inner actuation member 180 therethrough. Rotational motion imparted to the rotation knob 128 may thus impart rotational motion to each of the components of the elongated shaft 116, and to the end effector 114, which is coupled thereto. As shown in FIG. 12, the rotation knob 128 is seated within an interior compartment 134 of the housing 112 and, as shown in FIG. 1, extends laterally outward from opposing sides of the housing 112 (only shown extending laterally outward from housing half 112b).

Figure 5:
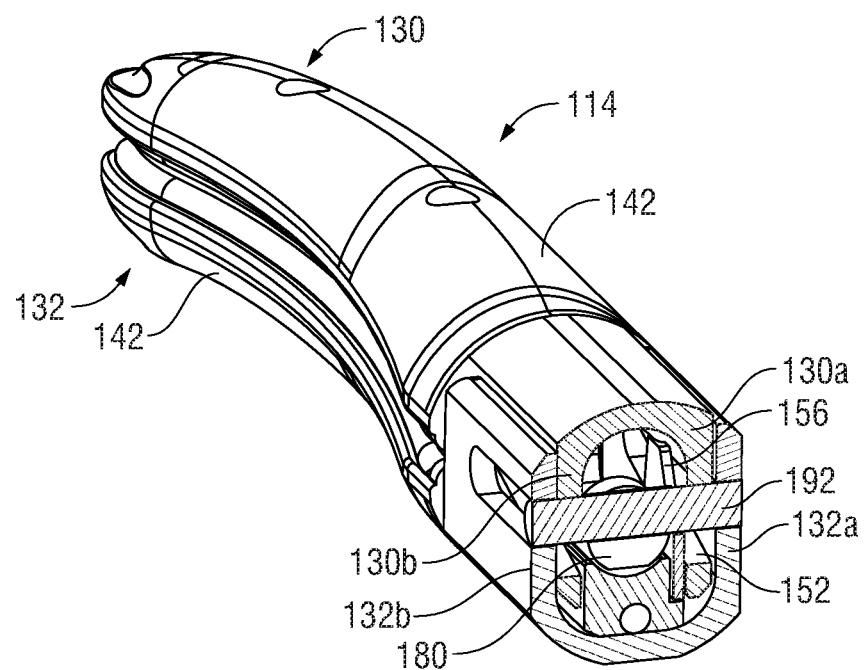
FIG. 5 is a cross-sectional, perspective view of the end effector of FIG. 1.

Referring now to FIG. 5, the end effector 114 is coupled to the distal end of the inner actuation member 180 by the cam pin 192. The cam pin 192 represents a longitudinally stationary reference for the longitudinal movements of the outer shaft member 160, the pivot pin 144, and the knife rod 102. The cam pin 192 extends through the flags 132a, 132b of the lower jaw member 132 and the flags 130a and 130b of the upper jaw member 130.

Figure 6:
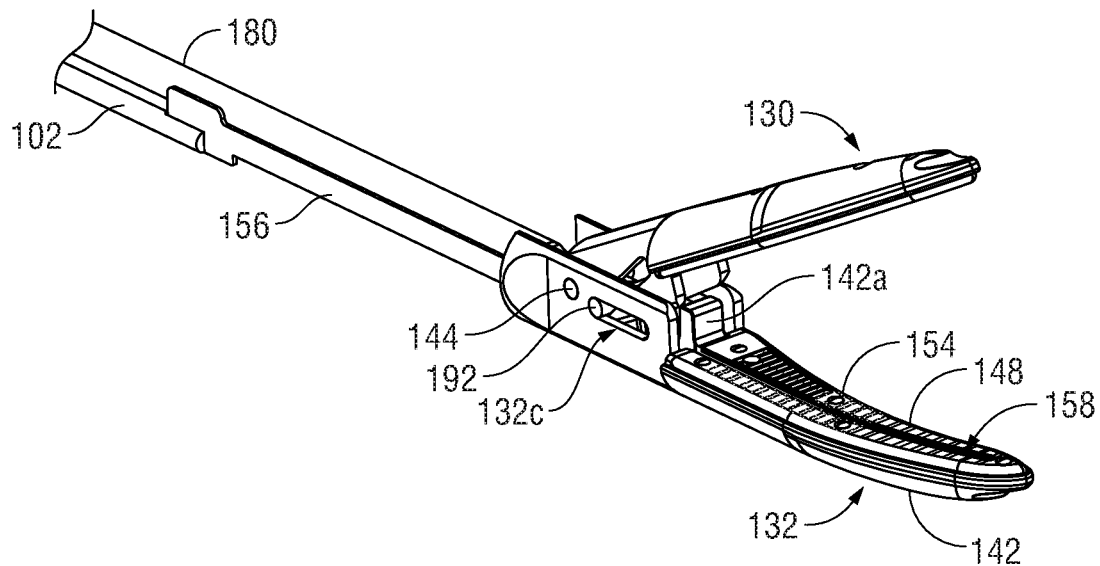
FIG. 6 is a partial, proximal-facing perspective view of a distal portion of a jaw actuation mechanism of the end effector of FIG. 1.

Referring now to FIG. 6, the end effector 114 is shown in the open configuration. Since the inner actuation member 180 is coupled to the cam pin 192, when the outer shaft member 160 is in the distal position (unactuated) and the inner actuation member 180 is in the proximal position relative to the outer shaft member 160, the cam pin 192 is located in a proximal position in cam slots 130c and 132c defined through the flags 130a, 130b, 132a, 132b of the jaw members 130, 132, respectively.

The outer shaft member 160 may be drawn proximally relative to the inner actuation member 180 and the cam pin 192 to move the end effector 114 to the closed configuration (see FIG. 2B). Since the longitudinal position of the cam pin 192 is fixed, and since the cam slots 130c, 132c are obliquely arranged with respect to the longitudinal axis A-A, proximal retraction of the outer shaft member 160 induces distal translation of the cam pin 192 through the cam slots 130c, 132c and jaw member 130 to pivot toward jaw member 132 about the pivot pin 144. Conversely, when the end effector 114 is in the closed configuration, longitudinal translation of the outer shaft member 160 in a distal direction induces proximal translation of the cam pin 192 through the cam slots 130c, 132c and jaw member 130 to pivot away from jaw member 132 toward the open configuration.

Figure 7:
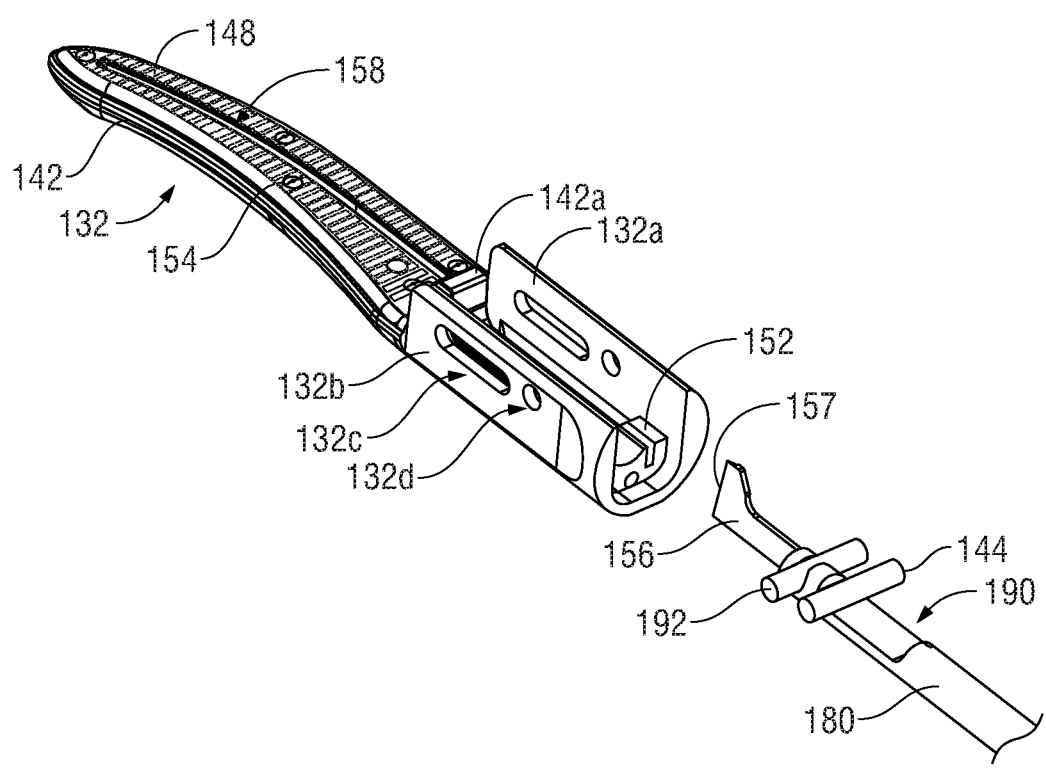
FIG. 7 is a partial, distal-facing perspective view of distal portion of a knife actuation mechanism of the end effector of FIG. 1.

Referring now to FIG. 7, the pins 144, 192 do not interfere with the reciprocal motion of the knife blade 156. A proximal portion of the insulator 142 forms a blade guide 142a (also see FIGS. 8 and 9) that serves to align the knife blade 156 such that the knife blade 156 readily enters the knife channel 158 defined in the jaw members 130, 132 (jaw member 130 removed from view in FIG. 7 for clarity).

Referring now to FIGS. 8 and 9, the lower jaw member 132 is constructed of three major components. These components include the jaw insert 140, the insulator 142, and the sealing plate 148. The flags 132a, 132b of the jaw member 132 define a proximal portion of the jaw insert 140 and a generally u-shaped profile of the jaw insert 140 extends distally to support the tissue engaging portion of the jaw member 132. Upper jaw member 130 includes the same three major components as lower jaw member 132, including sealing plate 150, and is constructed in the same manner as lower jaw member 132.

The insulator 142 may be constructed of an electrically insulative plastic such as a polyphthalamide (PPA) (e.g., Amodel®), polycarbonate (PC), acrylonitrile butadiene styrene (ABS), a blend of PC and ABS, nylon, ceramic, etc. The electrically insulative plastic may be overmolded onto the jaw insert 140 in a single-shot injection molding process such that sealing plate 148 is overmolded to the jaw insert 140. Additionally or alternatively, the electrically insulative plastic may be mechanically coupled to the jaw insert 140, e.g., pressed, snapped, glued, etc. Various features may be molded into the insulator 142 that facilitate the attachment of the sealing plate 148 to the insert 140. For example, tabs may be provided that permit a snap-fit attachment of the sealing plate 148, or ridges may formed that permit ultrasonic welding of the sealing plate 148 onto the insulator 142. The sealing plate 148 may be constructed of an electrically conductive metal, and may be stamped from a flat sheet stock.

Referring now to FIG. 10, the connection of the movable handle 122 and the knife trigger 126 to the longitudinally movable components of the elongated shaft 116 is described. The movable handle 122 may be manipulated to impart longitudinal motion to the outer shaft member 160, and the knife trigger 126 may be manipulated to impart longitudinal motion to the knife rod 102. As discussed above, longitudinal motion of the outer shaft member 160 serves to move the end effector 114 between the open configuration of FIG. 2A and the closed configuration of FIG. 2B, and longitudinal motion of the knife rod 102 serves to move knife blade 156 through knife channel 158 (FIG. 2A).

Figure 11:
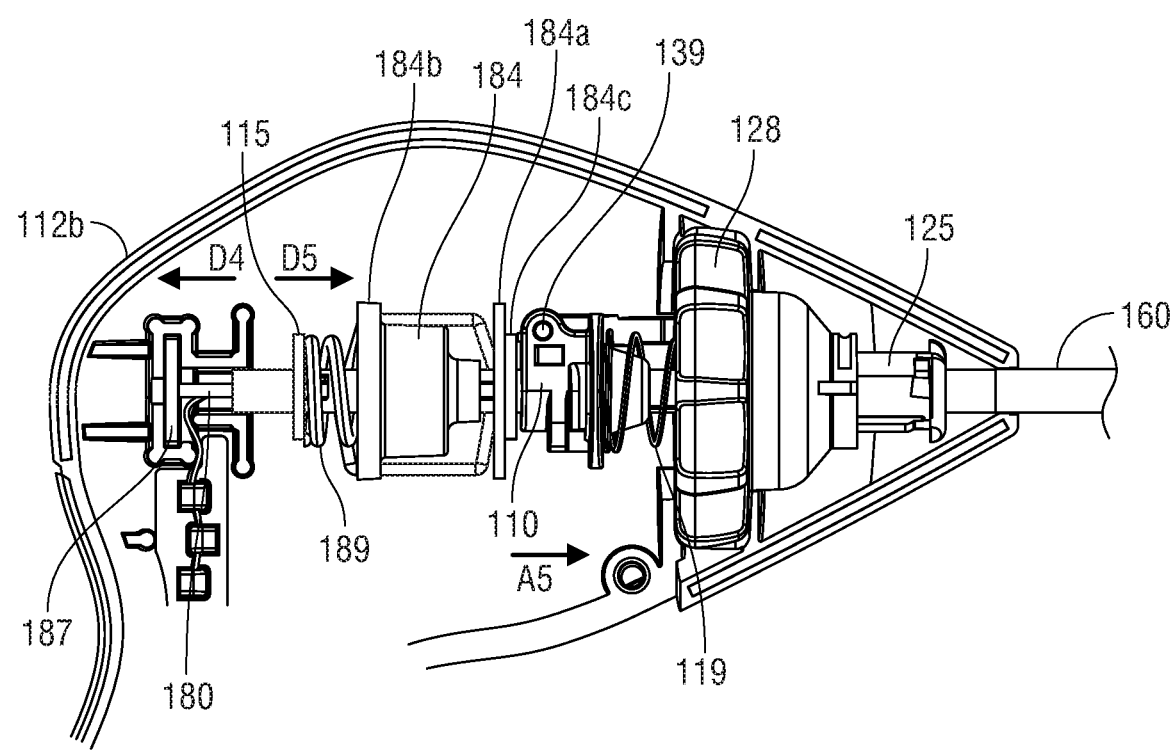
FIG. 11 is a partial, side view of a proximal portion of the instrument of FIG. 1.

The movable handle 122 is operatively coupled to the outer shaft member 160 by clevis 178 defined at an upper end of the movable handle 122. The clevis 178 is pivotally supported on the left housing half 112b by a pivot boss 179. A second complementary pivot boss (not shown) is provided on the right housing half 112a to support the clevis 178. The clevis 178 extends upwardly about opposing sides of a drive collar 184 (FIG. 11) supported on the outer shaft member 160 and includes drive surfaces or drive points 197a and 197b that may be asymmetrical relative to each other. Drive surface 197a engages a proximal-facing surface of a distal spring washer 184a and drive surface 197b engages a distal facing surface of a proximal rim 184b of the drive collar 184 (FIG. 11). The distal spring washer 184a engages a proximal facing surface of a distal spring stop 184c that, in turn, engages the opposing distal locking slots 161a, 161b (FIG. 3A) extending through the proximal portion 166 of the outer shaft member 160 to couple the distal spring stop 184c to the outer shaft member 160. A spring 189 is constrained between the proximal rim 184b and a proximal spring stop 115. The proximal spring stop 115 engages the opposing proximal locking slots 171a, 171b (FIG. 3A) extending through the proximal portion 166 of the outer shaft member 160 to couple the proximal lock collar 115 to the outer shaft member 160. The proximal lock collar 115 is biased distally by a leaf spring 117 disposed between the proximal lock collar 115 and a portion of the interior of the housing 112. The drive surfaces 197a, 197b are arranged along the longitudinal axis A-A such that pivotal motion of the movable handle 122 about the pivot bosses 179 induces corresponding longitudinal motion of the drive collar 184 along the longitudinal axis A-A.

Referring now to FIG. 11, proximal longitudinal motion may be imparted to the outer shaft member 160 by pushing the proximal rim 184b of the drive collar 184 proximally with the movable handle 122 (FIG. 10) as indicated by arrow D4 in FIG. 11 to move the jaw members 130, 132 to the closed configuration (FIG. 2B). The clevis 178 of the moveable handle 122 is shaped such that as the movable handle 122 pivots about the pivot boss 179 in the direction of arrow M1 (FIG. 13B), the drive surface 197b of the clevis 178 engages the proximal rim 184b of the drive collar 184. Once engaged, further pivoting of the moveable handle 122 about the pivot boss 179 in the direction of arrow M1 (FIG. 13B) causes the drive surface 197b to move the drive collar 184 proximally along the longitudinal axis A-A. Proximal movement of the drive collar 184 along the longitudinal axis A-A serves to separate the drive collar 184 from the distal spring washer 184a and compress the spring 189 between the proximal rim 184b and the proximal lock collar 115, as depicted in FIG. 13C, such that the outer shaft member 160 is driven proximally in the direction of arrow M2 (FIG. 13B). Compression of the spring 189 between the proximal rim 184b and the proximal lock collar 115 stores an elastic potential energy in the spring 189 such that the spring 189 imparts a spring force on the proximal rim 184b in the proximal direction to bias the moveable handle 122 toward a distal or unactuated position (FIG. 13A) against the pivoting force applied by a user on the moveable handle 122 in the direction depicted by arrow M1 (FIG. 13B).

Proximal longitudinal motion of the outer shaft member 160 draws jaw member 132 proximally such that the cam pin 192 advances distally to pivot jaw member 130 toward jaw member 132 to move the end effector 114 to the closed configuration as described above with reference to FIG. 6. Once the jaw members 130 and 132 are closed, the outer shaft member 160 essentially bottoms out (i.e., further proximal movement of the outer shaft member 160 is prohibited since the jaw members 130, 132 contact one another). Further proximal movement of the movable handle 122 (FIG. 10), however, will continue to move the drive collar 184 proximally. This continued proximal movement of the drive collar 184 further compresses the spring 189 to impart additional force to the outer shaft member 160, which results in additional closure force applied to tissue grasped between the jaw members 130, 132 (see FIG. 2B).

Distal longitudinal motion is imparted to the outer shaft member 160 by drawing the drive collar 184 distally with the movable handle 122 as indicated by arrow D4 (FIG. 11). As discussed above, the elastic potential energy stored in the spring 189 as a result of compression of the spring 189 between the proximal rim 184b and the proximal lock collar 115 imparts a spring force on the proximal rim 184b in the proximal direction. As the user releases the moveable handle 122 or otherwise decreases the pivoting force applied on the moveable handle 122 in the direction depicted by arrow M1 (FIG. 13B), the spring force applied by the spring 189 on the proximal rim 184b induces distal longitudinal motion of the drive collar 184 along the longitudinal axis A-A. Distal longitudinal motion of the drive collar 184 induces a corresponding distal motion of the outer shaft member 160 by virtue of the coupling of the drive collar 184 to opposing distal locking slots 181a, 181b extending through the proximal portion 166 of the outer shaft member 160 (FIG. 3A). Distal longitudinal motion of the outer shaft member 160 advances jaw member 132 distally such that the cam pin 192 advances proximally to pivot jaw member 130 away from jaw member 132 to move the end effector 114 to the open configuration as described above with reference to FIG. 6.

Referring again to FIG. 10, the trigger 126 is pivotally supported in the housing 112 about a pivot boss 103 protruding from the trigger 126. The trigger 126 is operatively coupled to the knife rod 102 by a knife connection mechanism 104 such that pivotal motion of the trigger 126 induces longitudinal motion of the knife rod 102. The knife connection mechanism 104 includes upper flanges 126a, 126b of the trigger 126 and a knife collar 110.

Referring now to FIGS. 11, 12A, and 12B, the knife collar 110 includes a pair of integrally formed pin bosses 139a, 139b extending from opposing sides thereof. As shown by FIG. 12B, the knife collar 110 includes an interior circular channel 113 that captures the angled proximal end 108 of the knife rod 102 to couple the knife rod 102 to the knife collar 110. Upon longitudinal motion of the outer shaft member 160, the angled proximal end 108 of the knife rod 102 translates longitudinally within the knife slot 168 of the outer shaft member 160 such that the longitudinal motion of outer shaft member 160 is unimpeded by the angled proximal end 108 of the knife rod 102. Upon rotation of the elongated shaft 116 and end effector 114 about the longitudinal axis A-A via the rotation knob 128 (FIG. 1), the angled proximal end 108 of the knife rod 102 freely rotates within the interior circular channel 113 of the knife collar 110 such that the outer and inner actuation members 160 and 180 (removed from view in FIG. 12B for clarity), and the knife rod 102 rotate within the knife collar 110 about the longitudinal axis A-A. In this way, the knife collar 110 serves as a stationary reference for the rotational movement of the outer shaft member 160, the inner actuation member 180, and the knife rod 102.

Referring again to FIG. 10, the upper flanges 126a, 126b of the trigger 126 include respective slots 127a, 127b defined therethrough that are configured to receive the pin bosses 139a, 139b, respectively, of the knife collar 110 such that pivotal motion of the trigger 126 induces longitudinal motion of the knife collar 110 and, thus, the knife rod 102 by virtue of the coupling of knife rod 102 to the knife collar 110.

Referring now to FIGS. 11 and 12A, when the trigger 126 is moved to induce motion of the knife collar 110 in order to translate the blade 156 through the knife channel 158, the knife collar 110 translates along the outer shaft member 160 in the direction of arrow A5 to abut a spring 119 such that spring 119 compresses against an interior portion of the rotation knob 128 (FIG. 10). The spring 119 biases the knife collar 110 proximally along the outer shaft member 160.

Referring now to FIGS. 13A, 13B, 13C and 13D, a sequence of motions may be initiated by moving the movable handle 122 to induce motion of the outer shaft member 160 in order to close the jaws 130, 132, and by moving the trigger 126 to induce motion of the knife collar 110 in order to translate the blade 156 through the knife channel 158. Initially, both the moveable handle 122 and the knife trigger 126 are in a distal or un-actuated position as depicted in FIG. 13A. This arrangement of the moveable handle 122 and trigger 126 sustains the end effector 114 in the open configuration (FIG. 2A) wherein the jaw members 130, 132 are substantially spaced from one another, and the knife blade 156 is in a retracted or proximal position with respect to the jaw members 130, 132. When both the moveable handle 122 and the knife trigger 126 are in the distal, un-actuated position, pivotal motion of the knife trigger 126 in a proximal direction, i.e., toward the stationary handle 120, is prohibited by interference between the trigger 126 and moveable handle 122. This interference prohibits advancement of the knife blade 156 through the knife channel 158 when the end effector 114 is in the open configuration.

The movable handle 122 may be moved from the distal position of FIG. 13A to the intermediate position depicted in FIG. 13B to move the jaw members 130, 132 to the closed configuration (FIG. 2B). As the movable handle 122 pivots about the pivot boss 179 in the direction of arrow M1 (FIG. 13B), the drive surface 197b of the movable handle 122 engages the proximal rim 184b of the drive collar 184. The drive collar 184 is driven proximally such that the spring 189 proximally biases the proximal lock collar 115 and, thus, the outer shaft member 160 is driven proximally in the direction of arrow M2 (FIG. 13B). As discussed above with reference to FIG. 6, proximal movement of the outer shaft member 160 serves to advance the cam pin 192 distally though the cam slots 130c, 132c of the jaw members 130, 132, respectively, and thus pivot jaw member 130 toward jaw member 132. As the jaw members 130, 132 engage one another and no further pivotal movement of the jaw members 130, 132 may be achieved, further proximal movement of the cam pin 192 and the outer shaft member 160 is prevented.

As the movable handle 122 is moved from the distal position of FIG. 13A to the intermediate position depicted in FIG. 13B, a tooth 122a extending proximally from an upper portion of the moveable handle 122 engages a clicker tab 120a supported within the stationary handle 120 to generate a tactile and/or audio response. This response generated by the clicker tab 120a corresponds to a complete grasping of tissue between the jaw members 130, 132 and serves to indicate to the surgeon that further proximal actuation of the moveable handle 122 will cause the button activation post 138 to engage the depressible button 137. As the moveable handle 122 is moved from the intermediate position of FIG. 13B to the actuated or proximal position of FIG. 13C, the tooth 122a is positioned proximally of the clicker tab 120a and the button activation post 138 depresses the depressible button 137, thereby activating the switch 136 disposed within the stationary handle 120 to initiate the delivery of electrosurgical energy to the end effector 114 to generate a tissue seal. In some embodiments, the switch 136 may be a two-stage switch or a multi-stage switch that switches the device 100 between two or multiple modes of energy delivery. For example, each stage of the switch 136 may effect delivery of a particular amount of electrosurgical energy to the end effector 114, different from the other stage(s).

As the movable handle 122 is moved from the intermediate position of FIG. 13B to the actuated or proximal position of FIG. 13C, the pressure applied by the jaw members 130, 132 is increased. As the movable handle 122 pivots further about the pivot boss 179 in the direction of arrow M3 (FIG. 13C), the drive surface 197b presses the proximal rim 184b of the drive collar 184 further proximally against the spring 189 in the direction of arrow M4 (FIG. 13C). The spring 189 is compressed against the proximal lock collar 115, and a tensile force is transmitted through the outer shaft member 160 to the jaw members 130, 132. The tensile force supplied by the spring 189 ensures that the jaw members 130, 132 apply an appropriate pressure to effect a tissue seal.

When the movable handle 122 is in the actuated or proximal position, the knife trigger 126 may be selectively moved from the distal position of FIG. 13C to the proximal position of FIG. 13D to advance the knife blade 156 distally through knife channel 158. The knife trigger 126 may be pivoted in the direction of arrow M5 (FIG. 13D), about pivot boss 103 to advance the flange 126b of the knife trigger 126 distally in the direction of arrow M6 such that the pin boss 139b translates within slot 127b from the position shown in FIGS. 13A-13C to the position shown in FIG. 13D. Although not explicitly shown in FIGS. 13A-13D, pin boss 139a translates within slot 127a in the same manner as described above with respect to pin boss 139b and slot 127b. Movement of flanges 126a, 126b draws the knife collar 110 distally, which induces distal longitudinal motion of the knife rod 102 by virtue of the coupling of the knife rod 102 to the knife collar 110, as described above with reference to FIG. 12B.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:
1. An electrosurgical instrument, comprising:
a housing;
an elongated shaft extending from the housing and defining a longitudinal axis;
a pair of jaw members disposed at a distal portion of the elongated shaft and configured to deliver electrosurgical energy to tissue;
a movable handle operably coupled to the housing and configured to move at least one of the pair of jaw members between an open position and a closed position; and
a drive collar movable along the longitudinal axis in response to movement of the movable handle, the movable handle including:
a first drive surface configured to impart a force on a portion of the drive collar that is disposed proximal to the first drive surface; and
a second drive surface configured to engage a washer disposed along the longitudinal axis, the drive collar configured to move proximally along the longitudinal axis to separate the drive collar from the washer upon movement of the movable handle.

2. The electrosurgical instrument according to claim 1, further comprising:
an actuation shaft axially disposed within the elongated shaft; and
a cam pin fixed to a distal portion of the actuation shaft.

3. The electrosurgical instrument according to claim 2, wherein at least one of the pair of jaw members defines a cam slot configured to receive the cam pin such that movement of the elongated shaft relative to the actuation shaft moves the at least one cam slot relative to the cam pin to move at least one of the pair of jaw members between the open and closed positions.

4. The electrosurgical instrument according to claim 1, wherein the washer is disposed distal to the second drive surface.

5. The electrosurgical instrument according to claim 1, wherein the second drive surface is disposed distal to the first drive surface.

6. The electrosurgical instrument according to claim 1, wherein proximal movement of the drive collar along the longitudinal axis moves at least one of the pair of jaw members toward the open position.

7. The electrosurgical instrument according to claim 1, wherein each of the pair of jaw members includes an electrically conductive tissue sealing plate.

8. The electrosurgical instrument according to claim 1, wherein the force imparted on the portion of the drive collar that is disposed proximal to the first drive surface compresses a spring disposed between a proximal stop operably coupled to a proximal portion of the elongated shaft and a proximal portion of the drive collar.

9. The electrosurgical instrument according to claim 8, wherein the spring is configured to bias at least one of the pair of jaw members toward the open position.

10. The electrosurgical instrument according to claim 1, further comprising a knife blade configured to move along the longitudinal axis to cut tissue disposed between the pair of jaw members.

11. The electrosurgical instrument according to claim 1, wherein at least one of the pair of jaw members defines a knife channel configured to receive a knife blade for cutting tissue disposed between the pair of jaw members.

12. The electrosurgical instrument according to claim 1, further comprising an activation button extending from the housing and configured to be actuated by the movable handle to control delivery of electrosurgical energy to the pair of jaw members.

13. The electrosurgical instrument according to claim 1, wherein the first and second drive surfaces are formed on a clevis defined by the movable handle, the clevis configured to couple the movable handle to the drive collar.

14. A drive assembly for actuating an end effector of an electrosurgical instrument, comprising:
  a movable handle configured to actuate an end effector; and
  a drive collar operably coupled to the movable handle and movable along a longitudinal axis defined by the electrosurgical instrument in response to movement of the movable handle, the movable handle including:
    a first drive surface configured to impart a force on a portion of the drive collar that is disposed proximal to the first drive surface; and
    a second drive surface configured to engage a washer disposed along the longitudinal axis, the drive collar configured to move proximally along the longitudinal axis to separate the drive collar from the washer upon movement of the movable handle to actuate the end effector.

15. The drive assembly according to claim 14, wherein the movable handle is operably coupled to a housing and the end effector is disposed at a distal portion of an elongated shaft extending from the housing.

16. The drive assembly according to claim 14, wherein the washer is disposed distal to the second drive surface.

17. The drive assembly according to claim 14, wherein the second drive surface is disposed distal to the first drive surface.

18. The drive assembly according to claim 14, wherein the force imparted on the portion of the drive collar that is disposed proximal to the first drive surface compresses a spring disposed between a proximal stop operably coupled to a proximal portion of the elongated shaft and a proximal portion of the drive collar.

19. The drive assembly according to claim 14, wherein the first and second drive surfaces are formed on a clevis defined by the movable handle, the clevis configured to couple the movable handle to the drive collar.

20. An electrosurgical instrument, comprising:
  a housing;
  an elongated shaft extending from the housing and defining a longitudinal axis;
  a pair of jaw members disposed at a distal portion of the elongated shaft and configured to deliver electrosurgical energy to tissue;
  a drive collar disposed within the housing and configured to move along the longitudinal axis; and
  a movable handle defining a clevis configured to couple the movable handle to the drive collar, the movable handle configured to move at least one of the pair of jaw members between an open position and a closed position, the clevis including:
    a first drive surface configured to impart a force on a portion of the drive collar that is disposed proximal to the first drive surface; and
  a second drive surface configured to engage a washer disposed along the longitudinal axis, the drive collar configured to move proximally along the longitudinal axis to separate the drive collar from the washer upon movement of the movable handle.

* * * * *